United States Patent [19]

Bellows et al.

[11] 4,308,874

[45] Jan. 5, 1982

[54] DIAGNOSIS OF EYE TUMORS

[75] Inventors: A. Robert Bellows, Topsfield; David Tapper, Newton, both of Mass.

[73] Assignee: The Children's Hospital Medical Center, Boston, Mass.

[21] Appl. No.: 118,848

[22] Filed: Feb. 5, 1980

[51] Int. Cl.³ .............................................. A61B 10/00
[52] U.S. Cl. ..................................... 128/745; 128/630
[58] Field of Search ................................ 128/745, 630

[56] References Cited

PUBLICATIONS

Brem, S. S. et al., *Cancer,* vol. 41, No. 1, Jan. 1978, pp. 239–244.
Tapper, D. et al., *Surgery,* vol. 86, No. 1, Jul.–Sep. 1979, pp. 36–40.
Finkelstein, D. et al., *Am. Journ. of Ophthalm.,* vol. 83, No. 5, Apr.–Jun. 1977, pp. 660–664.

*Primary Examiner*—Kyle L. Howell

[57] ABSTRACT

Malignant eye tumors are detected by extracting a specimen of aqueous humor from the eye and assaying it for angiogenesis capacity.

2 Claims, No Drawings

DIAGNOSIS OF EYE TUMORS

The invention described herein was made in the course or work under a grant or award from the Department of Health, Education and Welfare.

This invention relates to diagnosis of malignant eye tumors in mammals and pertains more specifically to a method for rapid and accurate detection of the early or incipient development of intraocular malignant tumors.

The diagnosis of malignant intraocular tumors is a difficult problem because one is limited to visual observation of the interior of the eye through the pupil, no biopsy of the suspected tissue being possible, and because a decision as to the necessity for enucleation of the eye must be made at as early a stage as possible to avoid metastasis.

There has previously been published a study on angiogenesis as an early marker in breast cancer: Brem et al., Cancer, Vol. 41, pages 239–244 (1978).

It has now been found that the presence of a malignant tumor within the mammalian eye can reliably be indicated by extracting a specimen of the aqueous humor from the eye in question, and assaying it for angiogenesis capacity. A positive indication of angiogenesis capacity is correlated with the presence of a malignant tumor within the eye.

The following specific examples are intended to illustrate more fully the nature of the invention without acting as a limitation upon its scope.

Aliquots (0.1 cc) of aqueous humor were aspirated from the anterior chamber of the eye of 36 human patients undergoing elective ophthalmologic surgery. The material was lyophylized and then implanted on the chorioallantoic membrane (C.A.M.) of 10-day old chick embryos by conventional procedures for bioassay. The identity and clinical condition of the patients were not known to those performing the assay. The angiogenesis capacity of each sample was graded negative or positive according to previously known procedures and standards as described, for example, in Br. J. Cancer, pages 35, 347 (1977). Nine out of 10 patients with retinoblastoma had a positive response by this test. Eight of these patients had no clinical evidence of neovascular changes or tumor cells in the anterior chamber of their eye. Seven of 11 patients with choroidal malignant melanoma had a positive response to their aqueous humor on the C.A.M. by this test. Aqueous samples from eyes with an iris and ciliary body malignant melanoma, and a metastatic breast carcinoma to the iris had a strongly positive angiogenic response. By contrast, 14 out of 15 patients undergoing surgery for cataracts, glaucoma, or other non-malignant ocular disease showed no positive angiogenesis capacity by this test. One patient who later developed lymphocytic leukemia had a positive assay. These intraocular tumors display angiogenesis capacity before clinically evident neovascular changes or floating tumor cells are seen. The positive yield for choroidal melanoma may be less than retinoblastoma because it is more often discontinuous with vitreous.

Other methods of assaying for angiogenesis capacity such as the rabbit eye test can also be used.

What is claimed is:

1. A method of detecting malignant tumors in mammalian eyes which comprises extracting a specimen of aqueous humor from an eye and assaying the specimen for angiogenesis capacity.

2. A method as claimed in claim 1 in which the eye is human.